(12) United States Patent
Feldman et al.

(10) Patent No.: US 7,993,505 B2
(45) Date of Patent: Aug. 9, 2011

(54) IN VITRO ANALYTE SENSOR AND METHODS OF USE

(75) Inventors: Benjamin J. Feldman, Oakland, CA (US); Yi Wang, San Ramon, CA (US)

(73) Assignee: Abbot Diabetes Care Inc., Alameda, CA (US)

( * ) Notice: Subject to any disclaimer, the term of this patent is extended or adjusted under 35 U.S.C. 154(b) by 0 days.

(21) Appl. No.: 12/463,213

(22) Filed: May 8, 2009

(65) Prior Publication Data

US 2009/0223837 A1 Sep. 10, 2009

Related U.S. Application Data

(63) Continuation of application No. 11/237,447, filed on Sep. 27, 2005, now Pat. No. 7,846,311.

(51) Int. Cl.
*G01N 27/327* (2006.01)
*G01N 27/416* (2006.01)

(52) U.S. Cl. ........... 204/403.01; 204/403.11; 205/777.5; 422/96

(58) Field of Classification Search ............ 204/403.01, 204/403.15, 409, 416, 418, 419, 403; 205/777.5, 205/778, 792; 600/345–348; 435/4–40.52; 422/68.1–98; 436/62–71, 500–548
See application file for complete search history.

(56) References Cited

U.S. PATENT DOCUMENTS

| | | | |
|---|---|---|---|
| 5,141,868 | A | 8/1992 | Shanks et al. |
| 5,496,453 | A | 3/1996 | Uenoyama et al. |
| 6,071,391 | A | 6/2000 | Gotoh et al. |
| 6,299,757 | B1 | 10/2001 | Feldman et al. |
| 6,338,790 | B1 | 1/2002 | Feldman et al. |
| 6,428,664 | B1 | 8/2002 | Bhullar et al. |
| 6,447,657 | B1 | 9/2002 | Bhullar et al. |
| 6,461,496 | B1 | 10/2002 | Feldman et al. |
| 6,572,745 | B2 | 6/2003 | Rappin et al. |
| 6,591,125 | B1 | 7/2003 | Buse et al. |
| 6,592,745 | B1 | 7/2003 | Feldman et al. |
| 6,618,934 | B1 | 9/2003 | Feldman et al. |
| 2002/0053523 | A1 * | 5/2002 | Liamos et al. ............... 205/787 |

FOREIGN PATENT DOCUMENTS

| | | |
|---|---|---|
| DE | 197 53 850 A1 | 6/1999 |
| DE | 203 14 395 U1 | 11/2003 |
| EP | 0 287 883 A1 | 10/1988 |
| EP | 0 422 708 A2 | 4/1991 |
| EP | 1 211 321 A1 | 6/2002 |
| WO | WO 97/00441 | 1/1997 |
| WO | WO 97/18464 | 5/1997 |
| WO | WO 98/43074 | 10/1998 |
| WO | WO 03/095092 A1 | 11/2003 |

* cited by examiner

*Primary Examiner* — Jeffrey T Barton
*Assistant Examiner* — Gurpreet Kaur
(74) *Attorney, Agent, or Firm* — Edward J. Baba; Khin K. Chin; Bozicevic, Field & Francis LLP

(57) ABSTRACT

In vitro electrochemical sensors that provide accurate and repeatable analysis of a sample of biological fluid are provided. Embodiments include sensors that include a sample chambers having overhangs extending therefrom.

35 Claims, 7 Drawing Sheets

IN VITRO ANALYTE SENSOR AND METHODS OF USE

CROSS-REFERENCE TO RELATED APPLICATIONS

This application is a continuation of U.S. patent application Ser. No. 11/237,447, filed on Sep. 27, 2005, now U.S. Pat. No. 7,846,311 which is incorporated herein by reference.

FIELD OF THE INVENTION

This invention relates to analytical sensors for the detection of analyte.

BACKGROUND OF THE INVENTION

Electrochemical analytical sensors are commonly used to determine the presence and concentration of a biological analyte. Such sensors are used, for example, to monitor blood glucose levels in diabetic patients.

Although many currently available sensor strip products require relatively large sample volumes, e.g., generally requiring 3 µL or more of blood or other biological fluid, there has been a trend for small volume sizes, such as 1 µL and less. For example, U.S. Pat. Nos. 6,143,164, 6,338,790 and 6,616,819 provide various configurations of small volume (i.e., less than 1 µL) sensors.

As the volume of sample chambers in the sensors decreases, it becomes increasingly more difficult to fill the sample chamber with the sample to be analyzed.

An attempt has been made, in U.S. Pat. No. 6,071,391, to provide an electrochemical sensor strip that easily receives the sample to be analyzed. The sample chamber is designed to be partially open at the peripheral part and partially closed by an internal adhesive layer.

As electrochemical sensors continue to be used, there continues to be an interest in electrochemical sensors that utilize a small sample volume of biological fluid for analysis and which are easy to fill with sample.

SUMMARY OF THE INVENTION

The electrochemical sensors of the present invention have a configuration that facilitates the filling of a sample chamber, particularly a small volume sample chamber. In some embodiments, the sample is maintained in a non-flowing manner in the sample chamber during analysis.

The sample chamber may be any suitable size, including large and small volume sample chambers. In certain embodiments, the sample chamber is sized to contain no more than about 1 µL (microliter) of sample, in some embodiments no more than about 0.5 µL, in some embodiments no more than about 0.25 µL, and in other embodiments no more than about 0.1 µL of sample, where in certain embodiments the sample chamber has a volume of no more than about 0.05 µL or even about 0.03 µL. A measurement zone is present within the sample chamber. The measurement zone may have the same volume, or less volume, than the sample chamber. The sample chamber may be substantially unbounded. For example, a percentage of the sample chamber perimeter may be unbounded, e.g., about 10% or more of the perimeter may be unbounded, e.g., about 50% or more of the perimeter may be unbounded, e.g., 70% or more, e.g., 80% or more, e.g., 90% or more, e.g., 95% or more of the perimeter may be unbounded. In certain embodiments, the sample chamber may be include linear sides and may be open to the atmosphere on at least one, two or more linear sides, e.g., three linear sides. For example, rectangularly shaped sample chambers have six linear sides and at least two or three of which may be unbounded and thus open to the outside environment. Having multiple sides open facilitates filling of the sample chamber with the sample to be analyzed. Capillary forces pull or otherwise facilitate filing of the sample chamber.

The sensors of the present invention are used for the detection and quantification of an analyte, for example glucose, where in many embodiments the detection and quantification is accomplished with a small volume, e.g., submicroliter sample. In general, the invention is a sensor for analysis of an analyte in an amount, e.g., small volume, of sample by, for example, coulometry, amperometry, potentiometry or any combination thereof. The sensors may also be suitable for use with photometry.

A sensor of the invention may utilize a non-leachable or non-diffusible or leachable or diffusible electron transfer agent, such as an enzyme. In many instances, the sensor may additionally or alternately utilize a non-leachable or non-diffusible or leachable or diffusible second electron transfer agent, such as a mediator, which can be a redox mediator.

Sensors of the present invention may include two substrates forming the overall sensor construction, a spacer between the substrates, a working electrode and at least one counter electrode. Together, the two substrates and spacer define a sample chamber between the substrates. At least a portion of the working electrode and counter electrode are present in the sample chamber. In accordance with embodiments of the invention, the substrates do not align at the sample receiving end or edge of the sensor; rather, at least one of the substrates extends past the end of the spacer. In other words, at least one substrate cantilevers out past the spacer. In some embodiments, both substrates extend past the end of the spacer, and, for example, one substrate may extend further than the other substrate. In many embodiments, the sensor may be in the shape of a strip or the like. The substrate overhang or cantilever is, in most embodiments, on the sample receiving end, side or edge of the sensor having the inlet to the sample chamber. In some embodiments, such as tip-filled sensor strips, the spacer cantilever is at the tip of the sensor strip.

These and various other features which characterize the invention are pointed out with particularity in the attached claims. For a better understanding of the sensors of the invention, their advantages, their use and objectives obtained by their use, reference should be made to the drawings and to the accompanying description, in which there is illustrated and described preferred embodiments of the invention.

BRIEF DESCRIPTION OF THE DRAWINGS

Referring now to the drawings, wherein like reference numerals and letters indicate corresponding structure throughout the several views.

DETAILED DESCRIPTION

Figure 1:
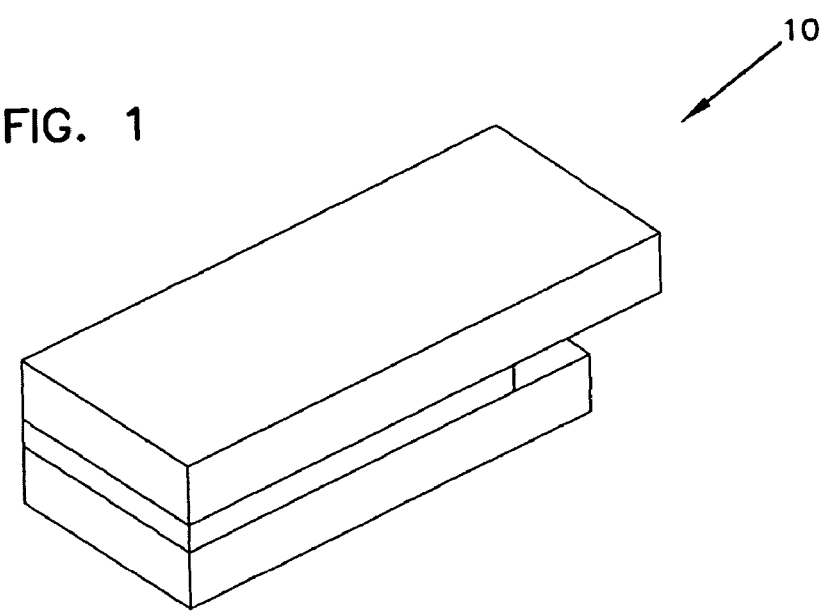
FIG. 1 is a schematic, perspective view of a first embodiment of an electrochemical sensor strip in accordance with the principles of the present invention.

When used herein, the following definitions define the stated term:

A "biological fluid" is any body fluid in which the analyte can be measured, for example, blood, interstitial fluid, dermal fluid, sweat, tears, and urine. "Blood" includes whole blood and its cell-free components, such as, plasma and serum.

A "counter electrode" refers to an electrode, used in conjunction with a working electrode, through which passes an electrochemical current equal in magnitude and opposite in sign to the current passed through the working electrode. The term "counter electrode" is meant to include counter electrodes which also function as reference electrodes (i.e. a counter/reference electrode) unless the description provides that a "counter electrode" excludes a reference or counter/reference electrode.

An "electrochemical sensor" or "electrochemical sensor strip", and variations thereof, is a device configured to detect the presence of and/or measure the concentration of an analyte via electrochemical oxidation and reduction reactions. These reactions are transduced to an electrical signal that can be correlated to an amount or concentration of analyte.

"Electrolysis" is the electrooxidation or electroreduction of a compound either directly at an electrode or via one or more electron transfer agents (e.g., redox mediators and/or enzymes).

An "electron transfer agent" is a molecule that carries electrons between either a redox mediator and the analyte or the working electrode and the analyte. An electron transfer agent may be used in combination with a redox mediator.

The term "facing electrodes" refers to a configuration of the working and counter electrodes in which the working surface of the working electrode is disposed in approximate opposition to a surface of the counter electrode.

An "indicator electrode" includes one or more electrodes that detect partial or complete filling of a sample chamber and/or measurement zone.

A "layer" includes one or more layers.

The "measurement zone" is defined herein as a region of the sample chamber sized to contain only that portion of the sample that is to be interrogated during an analyte assay.

A "non-diffusible," "non-leachable," or "non-releasable" compound is a compound which does not substantially diffuse away from the working surface of the working electrode for the duration of the analyte assay.

The term "planar electrodes" of "co-planar electrodes" refers to a configuration of the working and counter electrodes in which the working surface of the working electrode is disposed at least approximately planar to a surface of the counter electrode. "Planar electrodes" or "co-planar electrodes" are typically located on the same substrate.

A "redox mediator" is an agent for carrying electrons between the analyte and the working electrode, either directly, or via an electron transfer agent.

A "reference electrode" includes a reference electrode that also functions as a counter electrode (i.e., a counter/reference electrode) unless the description provides that a "reference electrode" excludes a counter/reference electrode.

A "working electrode" is an electrode at which analyte is electrooxidized or electroreduced with or without the agency of a redox mediator.

A "working surface" is the portion of a working electrode that is covered with non-leachable redox mediator and exposed to the sample, or, if the redox mediator is diffusible, a "working surface" is the portion of the working electrode that is exposed to the sample.

"Overhang" is the portion of a substrate that extends past or beyond another substrate. In many embodiments, the substrate that includes an overhang is a top substrate and the overhang is a longitudinally extending portion of the substrate.

The in vitro analyte sensors of the present invention may be designed to measure the concentration of an analyte in any volume of sample, but are particularly useful in the determination of analyte concentration in a small volume of sample, e.g., a sample having a volume no more than about 1 µL, for example no more than about 0.5 µL, for example no more than about 0.25 µL, and further for example no more than about 0.1 µL. In some embodiments, the volume of sample may be as low as 0.05 µL or as low as 0.03 µL. In some embodiments the biological fluid is blood, and the analyte of interest is glucose or lactate.

As summarized above, the sensors include two substrates separated by a spacer and in many embodiments the sensor has a cantilever configuration. The substrates, together with the spacer, form a sample chamber defined by the opposing surfaces of the top and bottom substrates and a front surface of the spacer (as will be described below). In many embodiments, one of the substrates (e.g., the top substrate) provides an overhang at the sample chamber end (sample filling end) of the substrate. This overhang provides an extension of the space that leads to the sample chamber, which may be a capillary space. The overhang may be provided by substrates of unequal lengths and/or substrates that are displaced along their longitudinal axes. In certain embodiments, the sample chamber is a capillary chamber and the overhang provides a capillary extension thereof to facilitate filling of the chamber by capillary action. The capillary chamber has a size suitable for filling by capillary action, and, in some embodiments, has only a single access port. That is, liquid sample ingress and gas (e.g., air) vent or egress are both via the same access port. An access port, whether for sample ingress, gas egress, or both, may have side that are curved or otherwise have a radius, or may be linear, e.g., having two or more (e.g., three) sides of a rectangle.

Referring to the Drawings in general and FIGS. 1-3 and 8 in particular, a first embodiment of an in vitro electrochemical sensor 10 of the invention is schematically illustrated, and which in this particular embodiment is a small volume sensor. Sensor 10 has a first substrate 12, a second substrate 14, and a spacer 15 positioned therebetween. As will be described below, sensor strip 10 includes at least one working electrode and at least one counter electrode. Sensor 10 is a layered construction, in this particular embodiment having a generally rectangular shape, i.e., its length is longer than its width, although other shapes are possible as well.

Figure 2:
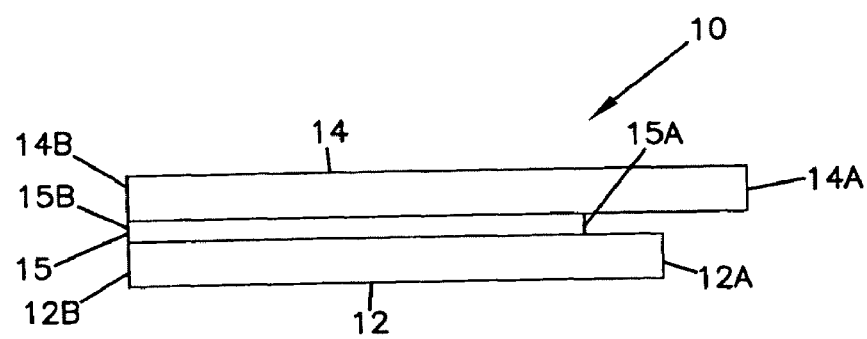
FIG. 2 is a side view of the sensor strip of FIG. 1.

Referring to FIG. 2, first or bottom substrate 12 has a first end 12A and an opposite second end 12B. Second or top substrate 14 has a first end 14A and an opposite second end 14B. Spacer 15 has a first or front (sample filling) end 15A and an opposite second end 15B. For this disclosure, first ends 12A, 14A, 15A are considered the "distal end" and second ends 12B, 14B, 15B are considered the "proximal end". As will be described in detail below, at the distal end of sensor strip 10, substrate first end 12A and substrate first end 14A are intentionally not aligned. That is, first substrate end 12A and second substrate end 14A are intentionally displaced from one another so that a portion of the second substrate extends beyond end 12A of the first substrate in the direction of the longitudinal axis of the sensor. In this embodiment illustrated, spacer end 15A is also not aligned with either end 12A, 14A; that is, spacer end 15A is displaced from both substrate end 12A and substrate end 14A. As described in greater detail below, this displacement of the substrate(s) relative to each other provides an overhang 17.

The dimensions of a sensor may vary. In certain embodiments, the overall length of sensor strip 10 may be no less than about 20 mm and no greater than about 50 mm. For example, the length may be between about 30 and 45 mm; e.g., about 30 to 40 mm. It is understood, however, that shorter and longer sensor strips 10 could be made. In certain embodiments, the overall width of sensor strip 10 may be no less than about 3 mm and no greater than about 15 mm. For example, the width may be between about 4 and 10 mm, about 5 to 8 mm, or about 5 to 6 mm. In one particular example, sensor strip 10 has a length of about 32 mm and a width of about 6 mm. In another particular example, sensor strip 10 has a length of about 40 mm and a width of about 5 mm. In yet another particular example, sensor strip 10 has a length of about 34 mm and a width of about 5 mm.

Substrates

As provided above, sensor strip 10 has first and second substrates 12, 14, non-conducting, inert substrates which form the overall shape and size of sensor strip 10. Substrates 12, 14 may be substantially rigid or substantially flexible. In certain embodiments, substrates 12, 14 are flexible or deformable. Examples of suitable materials for substrates 12, 14 include, but are not limited to, polyester, polyethylene, polycarbonate, polypropylene, nylon, and other "plastics" or polymers. In certain embodiments the substrate material is "Melinex" polyester. Other non-conducting materials may also be used.

Figure 3:
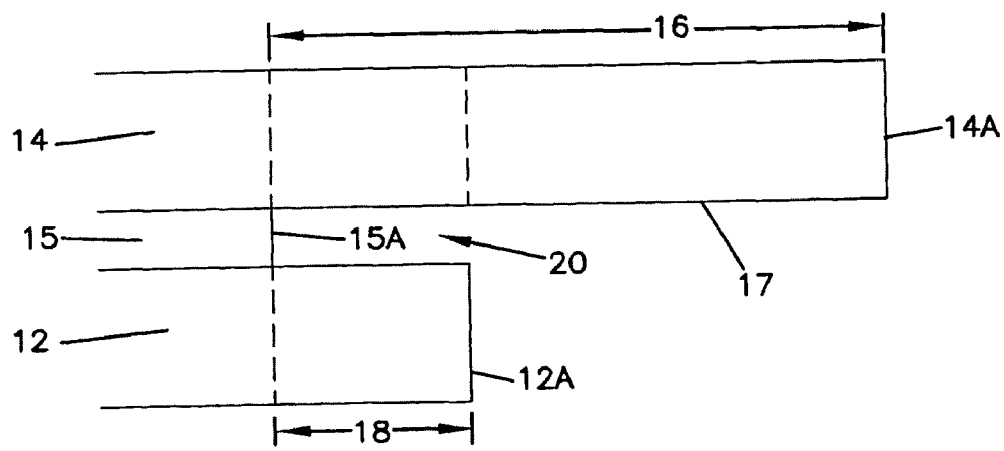
FIG. 3 is an enlarged view of a first end of the sensor strip of FIGS. 1 and 2.

In this embodiment illustrated in FIGS. 1 through 3, substrate 14, when measured from first end 14A to second end 14B, is longer than substrate 12, from first end 12A to second end 12B, the additional length of substrate 14 providing overhang 17. In many embodiments, the length of substrate 12, from first end 12A to second end 12B, is no less than about 8 mm and no greater than about 48 mm, e.g., between about 28 mm and about 38 mm, and for example, may be about 30 to about 35 mm. In one example, the length is about 31 mm. In many embodiments, the length of substrate 14, from first end 14A to second end 14B, is no less than about 10 mm and no greater than about 50 mm, e.g., the length is between about 30 and about 45 mm. In one example, the length is about 32 mm. The width of substrates 12, 14 may be the same or different, and in many embodiments will be the same, which may be no less than about 1 mm and no greater than about 15 mm in certain embodiments, e.g., about 2-5 mm. The thickness of substrates 12, 14 may be the same or different and may vary, wherein certain embodiments the thickness may be at least about 0.05 mm and generally no greater than about 3 mm, e.g., between about 0.20 and about 2 mm. In certain embodiments the thickness is about 0.25 mm.

It is understood that both shorter and longer lengths for either or both substrate 12 and substrate 14 could be used, as can wider and/or thicker substrates 12, 14.

Spacer Layer

As indicated above, positioned between substrate 12 and substrate 14 is spacer 15. Spacer 15 separates first substrate 12 from second substrate 14. Spacer 15 is an inert non-conducting substrate, typically at least as flexible and deformable (or as rigid) as substrates 12, 14. In certain embodiments, spacer 15 is an adhesive layer or double-sided adhesive tape or film. Any adhesive selected for spacer 15 should be selected to prevent or minimize diffusion or the release of material which may interfere with accurate analyte measurement.

The thickness of spacer 15 defines the depth of the sample chamber and may be dimensioned to provide a sample chamber having a capillary volume. In certain embodiments, the thickness of spacer 15 may be at least about 0.01 mm (10 μm) and no greater than about 1 mm or about 0.5 mm. For example, the thickness may be between about 0.02 mm (20 μm) and about 0.2 mm (200 μm). In one certain embodiment, the thickness is about 0.05 mm (50 μm), and about 0.1 mm (100 μm) in another embodiment.

The length of spacer 15 may be less than the length of substrate 12 and/or of substrate 14, and/or the spacer and one or both substrates may be displaced along their longitudinal axes. As will be described in detail below, first end 15A of spacer 15 does not align with first ends 12A, 14A, but is recessed. Second end 15B may or may not be aligned with either second end 12B, 14B. The width of spacer 15 may be the same or different than the widths of the substrates, where in many embodiments the width is generally the same as the width of substrate 12 and substrate 14.

Substrate Overhang

As mentioned above, in accordance with various embodiments of the present invention, second substrate 14 extends past spacer 15 at the distal end; in particular, first end 14A extends past first end 15A; this length of cantilevered substrate is indicated in FIG. 3 by reference number 16. First substrate 12 extends past spacer 15 at the distal end; in particular first end 12A extends past first end 15A; this length of extension is indicated in FIG. 3 by reference number 18.

Additionally, second substrate 14 overhangs past first substrate 12 at the distal end; in particular, first end 14A overhangs or extends past first end 12A. This overhang is represented by reference number 17, and is the length of cantilever 16 less extension 18. The dashed lines are included in FIG. 3 to aid in alignment of the various features discussed herein. In the embodiment illustrated, there is no other sensor strip 10 structure positioned above or below overhang 17 of substrate 14.

The dimensions of cantilever 16 may vary. For ease of description, cantilever 16 may be characterized with respect to the overall length of sensor 10. For example, cantilever 16 may range from about 0.05% to about 50% of the length of sensor 10, e.g., from about 1% to about 20% of the length of sensor 10, e.g., from about 4% to about 10%, e.g., about 6% of the length of sensor 10, although larger and smaller overhangs could be used. Cantilever 16 may have a length of, or in other words, second substrate 14 may extend past spacer layer 15 by at least about 0.25 mm, e.g., at least about 0.5 mm, or e.g., at least about 1 mm. In certain embodiments, cantilever 16 may be no more than about 20 mm. A cantilever 16 of about 2 mm is one specific example.

The dimensions of extension 18 may vary. For ease of description, extension 18 may be characterized with respect to the overall length of sensor 10. For example, extension 18 may range from about 0.05% to about 50% of the length of sensor 10, e.g., from about 1% to about 20% of the length of sensor 10, e.g., from about 4% to about 10%, e.g., about 4% of the length of sensor 10, although larger and smaller extensions could be used. Extension 18 may have a length of, or in other words, first substrate 14 may extend past spacer layer 15 by, at least about 0.25 mm, e.g., at least about 0.5 mm, or e.g., at least about 1 mm. In certain embodiments, extension 18 may be no more than about 20 mm. An extension 18 of about 1 mm is one specific example.

As provided above, the distance second substrate 14 extends past or overhangs first substrate 12 is referred to herein as overhang 17. In some embodiments, the length of overhang 17 is zero; that is, the length of cantilever 16 is the same as the length of extension 18. In those embodiments in which an overhang is present, the dimensions of the overhang may vary. In certain embodiments, the overhang is dimensioned to provide a capillary chamber, with a skin surface providing a wall of the thus-formed overhang capillary chamber, to draw, using capillary forces, sample into sample chamber 20. Accordingly, in certain embodiments the overhang may be sized to provide a capillary space having capillary volume, defined by a surface of cantilever 16 and an opposing surface such as the skin of the user when positioned in opposition thereto. The capillary volume may range from about 10 nL (0.01 µL) to about 10,000 mL (10 µL), e.g., about 100 nL (0.1 µL) to about 1000 nL (1 µL), e.g., from about 200 nL (0.2 µL) to about 500 nL (0.5 µL). As shown, the overhang and thus the capillary chamber formed by the overhang are in fluid communication with the sample chamber so that sample contacted with the overhang flows into the sample chamber.

The exact dimensions of overhang 17 may vary. For ease of description, one way to characterize overhang 17 is with respect to the overall length of sensor 10. For example, overhang 17 may range from about 0.5% to about 20% of the overall length of strip 10, e.g., 1% to about 10%, e.g., 2% to about 5%, e.g., 3% the length of strip 10. In certain embodiments, overhang 17 may be at least about 0.1 mm, and in some embodiments, at least about 0.25 mm, at least about 0.5 mm, and in some other embodiments, at least about 1 mm. In certain embodiments, overhang 17 may be no more than about 10 mm, e.g., no more than about 5 mm, e.g., 1 mm, e.g., about 0.25 mm to about 0.5 mm, where an overhang may be about 0.1 mm in certain embodiments.

Cantilever 16 may be equal to or greater than extension; that is, the ratio of cantilever 16: extension 18 may be at least about 1:1. In certain embodiments, the ratio of cantilever 16: extension 18 maybe at least about 1.5:1 and maybe at least about 2:1. The ratio of cantilever 16: extension 18 may be no more than about 10:1 and in some embodiment no more than about 5:1. In one example, extension 18 is about 1 mm and cantilever 16 is about 2 mm; extension 18 is half of cantilever 16, which is a ratio of cantilever 16: extension 18 of 2:1.

In some embodiments, overhang 17 may be about equal to extension 18; that is the ratio of overhang 17: extension 18 may be about 1:1. In some other embodiments, overhang 17 may be equal to about half, or about 50%, of cantilever 16; that is, the ratio of overhang 17: cantilever 16 may be about 1:2. In still further embodiments, cantilever 16 my be about twice that of extension 18 (ratio of about 2:1), thus overhang 17 may be about half of cantilever 16 (ratio of about 1:2) and about equal to extension 18 (ratio of about 1:1).

Overhang 17 has a sample contacting surface area (i.e., the surface area of the surface of the overhang that comes in contact with sample) associated therewith, which is the distance or length of overhang x the width of overhang 17 (which in most embodiments is the width of substrate 14 and/or sensor strip 10). In certain embodiments, the surface area of overhang 17 may be at least about 0.1 $mm^2$ and no greater than about 1 $cm^2$, e.g., about 2 $mm^2$ to about 30 $mm^2$, e.g., about 5 $mm^2$ to about 10 $mm^2$. In some embodiments, the surface area of overhang 17 may be about 1 $mm^2$ to about 5 $mm^2$.

In many embodiments, second ends 12B and 14B are generally aligned; that is, neither end 12B, 14B extends or overhangs the other. If there is an overhang, it may be no more than about 2 mm in certain embodiments. There are some embodiments where a misalignment or overhang exists at second end 12B, 14B. For example, second ends 12B, 14B may include an overhang, tab, indent, or otherwise be configured for connecting to a meter. For the description of sensor strip 10 herein, and of substrates 12, 14, it is assumed that second ends 12B, 14B align. Thus, when there is discussion that one substrate is longer than another, it is assumed that second ends 12B, 14B are aligned, so that the opposite ends, ends 12A, 14A, are not aligned. Spacer end 15B also is generally aligned with ends 12B, 14B.

Sample Chamber

Figure 8:
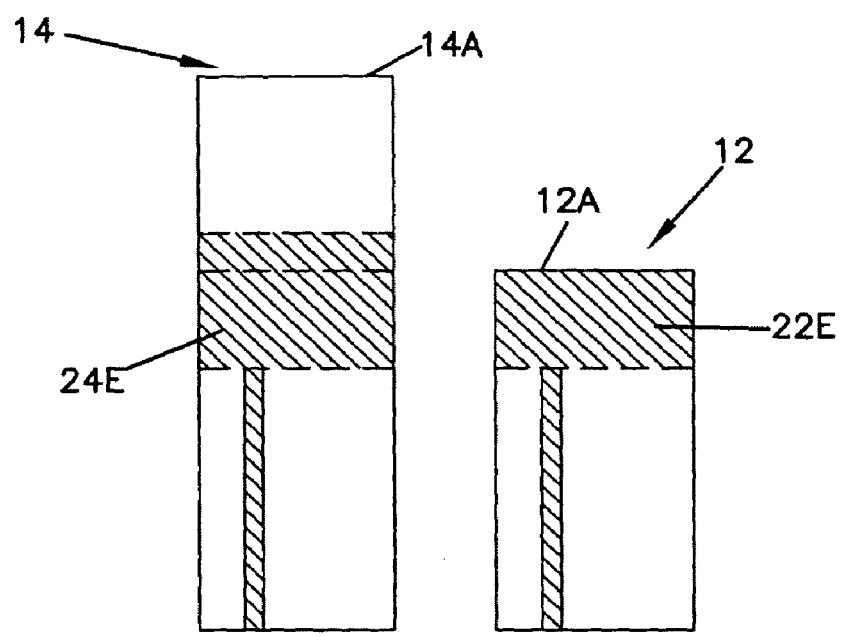
FIG. 8 is a top view of a fifth embodiment of an electrode configuration for a sensor strip according to the invention, the sensor strip illustrated disassembled, configured to have a working electrode and a counter electrode planar when assembled.
Figure 10:
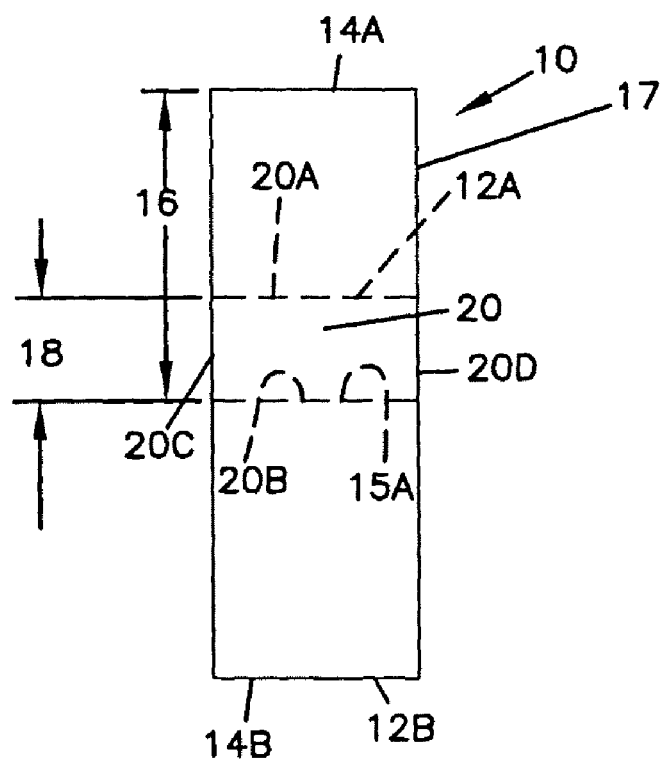
FIG. 10 is a top view of the sensor strip of FIGS. 1, 2 and 3.

Still referring to FIG. 3 and also to FIG. 10, sensor strip 10 includes a sample chamber 20 for receiving a volume of sample to be analyzed. Sample chamber 20 is configured so that when a sample is provided in chamber 20, the sample is in electrolytic contact with both the working electrode and the counter electrode, which allows electrical current to flow between the electrodes to effect the electrolysis (electrooxidation or electroreduction) of the analyte. In the embodiment of FIGS. 3 and 8, sensor strip 10 is configured to receive a sample into sample chamber 20 at the distal end of sensor strip 10; this distal end is the sample receiving end of sensor strip 10.

As noted above, sample chamber 20 is defined, in part, by substrate 12, substrate 14 and by first or distal end 15A of spacer 15. Extension 18 is the portion of substrate 12 that defines sample chamber 20 and the portion of cantilever 16 of substrate 14 that is not part of overhang 17 also defines sample chamber 20. Accordingly, overhang 17 extends from, and is in communication with, sample chamber 20. As shown, a portion of the sample chamber perimeter is open or unbounded, where in certain embodiments a substantial portion is unbounded, equal to or greater than a majority of the perimeter of the sample chamber. For example, a percentage of the sample chamber perimeter may be unbounded, e.g., about 10% or more of the perimeter may be unbounded, e.g., about 50% or more of the perimeter may be unbounded, e.g., 70% or more, e.g., 80% or more, e.g., 90% or more, e.g., 95% or more of the perimeter may be unbounded.

As shown in the Figures, this particular sample chamber may be characterized as having sides such that three elements, substrate 12, substrate 14 and first end 15A, define three sides of sample chamber 20. At least one other side of sample chamber 20 is open, and in this embodiment, three other sides of sample chamber 20 are open.

Referring to FIG. 10, a top view of sensor strip 10 is illustrated. From this view, sample chamber 20 has sides 20A, 20B, 20C, 20D. Sides 20A, 20C and 20D are open to the atmosphere, that is, they are not bounded. Side 20A is defined as the location where first substrate 12 terminates at first end 12A. Side 20B is defined by first end 15A of the spacer. Sides 20C, 20D are aligned with the side edges of substrates 12, 14. It is understood that in other embodiments, sample chambers may be designed that have, e.g., more sides, less sides, curved sides, or otherwise differ from sample chamber 20.

Sample chamber 20 has a volume sufficient to receive a sample of biological fluid therein. In some embodiments, such as when sensor strip 10 is a small volume sensor, sample chamber 20 has a volume that is no more than about 1 µL, for example no more than about 0.5 µL, and also for example, no more than about 0.25 µL. A volume of no more than about 0.1 µL is also suitable for sample chamber 20, as are volumes of no more than about 0.05 µL and no more than about 0.03 µL. Sample chamber 20 has dimensions that facilitate drawing sample to be analyzed into sample chamber 20 by capillary or other surface tensions forces. In embodiments that include spacer 15 between substrates 12, 14, the thickness of sample chamber 20 is generally the thickness of spacer 15.

A measurement zone is contained within sample chamber 20 and is the region of the sample chamber that contains only that portion of the sample that is interrogated during the analyte assay. In some embodiments, the measurement zone has a volume that is approximately equal to the volume of sample chamber 20. In some embodiments the measurement zone includes 100% of the sample chamber or less, e.g., 80% or less, e.g., 75% or less. In certain embodiments, the sample chamber is a partial fill sample chamber, as described in co-pending application titled "In vitro Analyte Sensor, and Methods" filed Sep. 12, 2005, attorney docket no. 12008.88US01.

Electrodes

As provided above, sensor strip 10 includes a working electrode and at least one counter electrode. The counter electrode may be a counter/reference electrode. If multiple counter electrodes are present, one of the counter electrodes will be a counter electrode and one or more may be reference electrodes. Referring to FIGS. 4 through 9, six examples of suitable electrode configurations are illustrated.

Working Electrode

Figure 4:
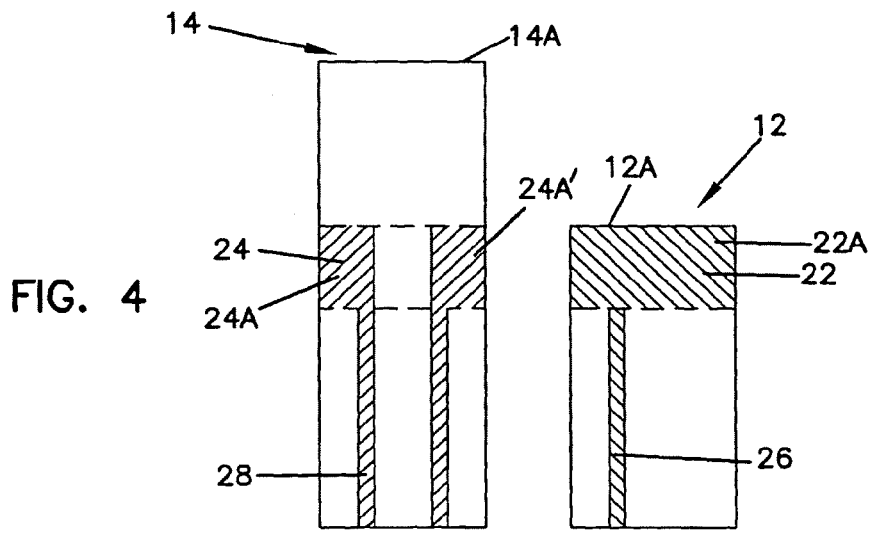
FIG. 4 is a top view of a first embodiment of an electrode configuration for a sensor strip according to the invention, the sensor strip illustrated disassembled, configured to have a working electrode and two counter electrodes facing each other when assembled.

At least one working electrode is positioned on one of first substrate 12 or second substrate 14. Referring to FIG. 4, working electrode 22 is illustrated on substrate 12. Working electrode 22 includes a conductive trace 26 extending to the proximal end, such as for connecting to a meter.

Working electrode 22 can be a layer of conductive material such as gold, carbon, platinum, ruthenium dioxide, palladium, or other non-corroding, conducting material. An example of a suitable conductive epoxy is ECCOCOAT CT5079-3 Carbon-Filled Conductive Epoxy Coating (available from W.R. Grace Company, Woburn, Mass.).

Working electrode 22 may be applied on substrate 12 by any of various methods. Electrode 22 may be deposited, such as by vapor deposition or vacuum deposition, sputtered, printed on a flat surface or in an embossed or otherwise recessed surface, transferred from a separate carrier or liner, etched, or molded. Screen-printing is a suitable method for applying working electrode 22, although other methods such as piezoelectric printing, ink jet printing, laser printing, photolithography, and painting can be used.

The material of working electrode 22 typically has relatively low electrical resistance and is typically electrochemically inert over the potential range of the sensor during operation.

Working electrode 22 is provided in sample chamber 20 for the analysis of analyte, in conjunction with the counter electrode, as will be described below.

Counter Electrode

Sensor strip 10 typically includes at least one counter electrode positioned within sample chamber 20 on substrate 12 or 14. Referring to FIG. 4, two counter electrodes 24 are illustrated on substrate 14. Each counter electrode 24 includes a conductive trace 28 extending to the proximal end, such as for connecting to a meter.

Counter electrode 24 may be constructed in a manner similar to working electrode 22. Counter electrode 24 may also be a counter/reference electrode.

Alternatively, a separate reference electrode may be provided in contact with the sample chamber. Suitable materials for the counter/reference or reference electrode include Ag/AgCl or Ag/AgBr applied (e.g., printed) on a non-conducting base material or silver chloride on a silver metal base. The same materials and methods may be used to make counter electrode 24 as are available for constructing working electrode 22, although different materials and methods may also be used. Counter electrode 24 can include a mix of multiple conducting materials, such as Ag/AgCl and carbon.

Electrode Configurations

Working electrode 22 and counter electrode 24 may be disposed opposite to and facing each other to form facing electrodes. Referring to FIG. 4, working electrode 25 22, specifically working electrode 22A, occupies the surface of substrate 12 that corresponds to sample chamber 20. Counter electrodes 24, specifically counter electrodes 24A, 24A', together, occupy less than the total surface of substrate 14 that corresponds to sample chamber 20. When assembled, working electrode 22A overlaps each of counter electrodes 24A, 24A', forming facing electrodes.

Figure 5:
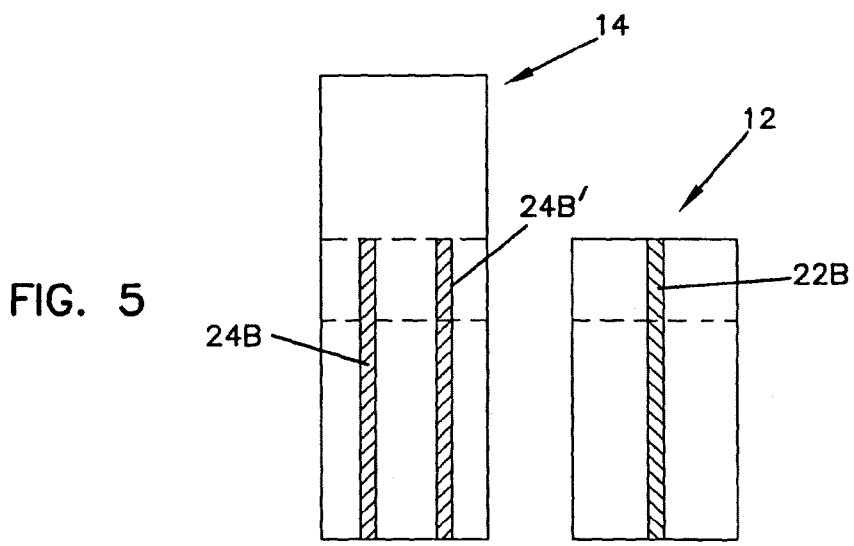
FIG. 5 is a top view of a second embodiment of an electrode configuration for a sensor strip according to the invention, the sensor strip illustrated disassembled, configured to have a working electrode and two counter electrodes facing each other when assembled.

Referring to FIG. 5, a second facing electrode configuration is illustrated. Working electrode 22B occupies an area on substrate 12 significantly less than that which corresponds to sample chamber 20. Counter electrodes 24B, 24B', together, occupy significantly less than the total surface of substrate 14 that corresponds to sample chamber 20. Working electrode 22B is generally equally spaced between the two counter electrodes 24B, 24B' but, when assembled, working electrode 22B does not directly overlap counter electrodes 24B, 24B'.

Figure 7:
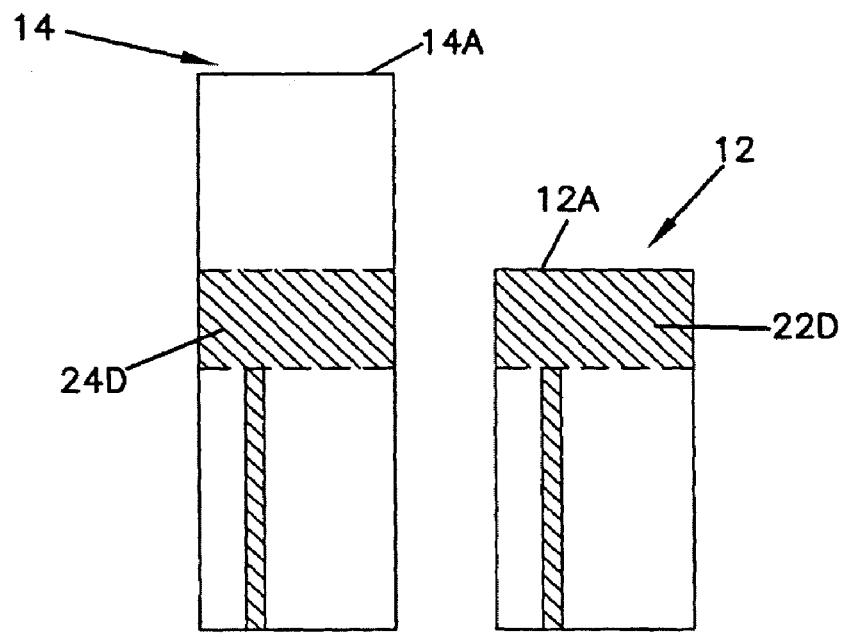
FIG. 7 is a top view of a fourth embodiment of an electrode configuration for a sensor strip according to the invention, the sensor strip illustrated disassembled, configured to have a working electrode and a counter electrode planar when assembled.

Referring to FIG. 7, a third facing electrode configuration is illustrated. Working electrode 22D, occupies the surface of substrate 12 that corresponds to sample chamber 20. Counter electrodes 24D occupies the surface of substrate 14 that corresponds to sample chamber 20. When assembled, working electrode 22D overlaps counter electrode 24D, forming facing electrodes.

Referring to FIG. 8, a fourth facing electrode configuration is illustrated. Working electrode 22E occupies the surface of substrate 12 that corresponds to sample chamber 20. Counter electrodes 24E occupies the surface of substrate 14 that corresponds to sample chamber 20 and additional area of substrate 14 outside of sample chamber 20. When assembled, working electrode 22E overlaps counter electrode 24E, forming facing electrodes.

Figure 9:
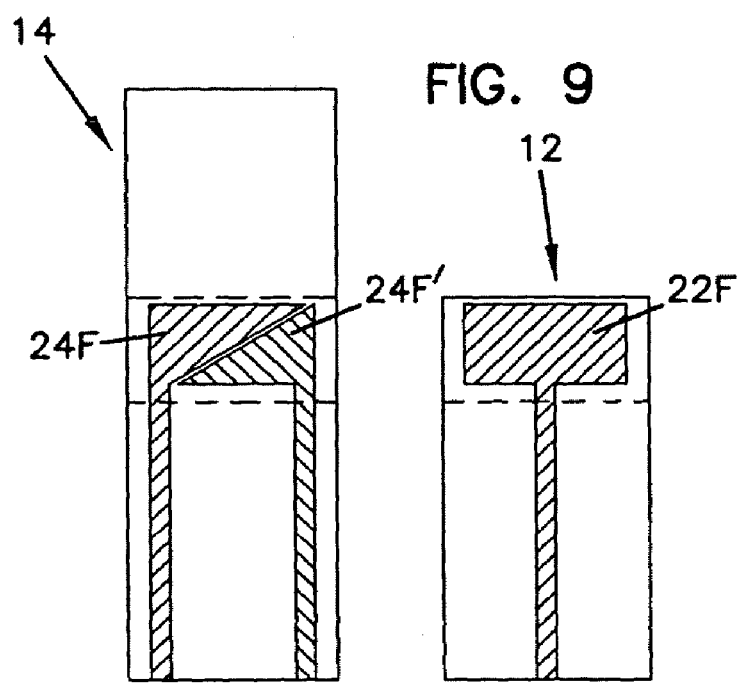
FIG. 9 is a top view of a sixth embodiment of an electrode configuration for a sensor strip according to the invention, the sensor strip illustrated disassembled, configured to have a working electrode and a counter electrode planar when assembled.

Referring to FIG. 9, a fifth facing electrode configuration is illustrated. Working electrode 22F occupies the surface of substrate 12 that corresponds to sample chamber 20. Each of two counter electrodes 24F, 24F' occupy approximately half of the area on substrate 14 that corresponds to sample chamber 20. Together, electrodes 24F, 24F' occupy almost the total surface of substrate 14 that corresponds to sample chamber 20.

Figure 6:
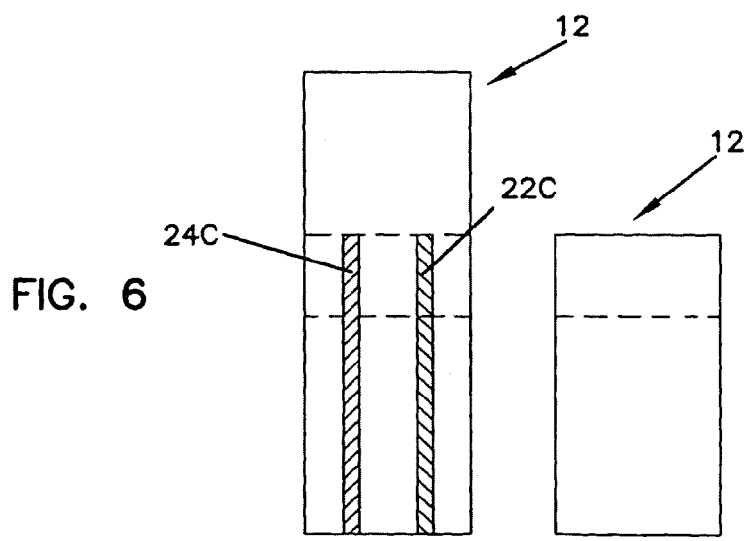
FIG. 6 is a top view of a third embodiment of an electrode configuration for a sensor strip according to the invention, the sensor strip illustrated disassembled, configured to have a working electrode and a counter electrode planar when assembled.

Working electrode 22 and counter electrode 24 can alternately be disposed generally planar to one another, such as on the same substrate, to form co-planar or planar electrodes. Referring to FIG. 6, both working electrode 22C and counter electrode 24C occupy a portion of the surface of substrate 14 that corresponds to sample chamber 20, thus forming co-planar electrodes. In the configurations of FIG. 6, there is no reference electrode or counter/reference electrode, and there is no structure on substrate 12.

As illustrated in FIGS. 4 through 9, the electrodes may be facing or co-planar, and facing electrodes need not be directly opposing each other. The electrodes may or may not cover the entire area of substrate 12, 14. Furthermore, the electrodes need not be the same size.

It is noted that each of the electrodes illustrated include a conductive trace connecting the electrode to the proximal end of the sensor; such traces are used for connecting the electrode to a meter.

Additionally, although not illustrated in FIGS. 4 through 9, sensor strip 10 may include a fill indicator electrode, to determine when the sample chamber is sufficiently filled with sample.

Alternative Sensor Designs

Figure 11:
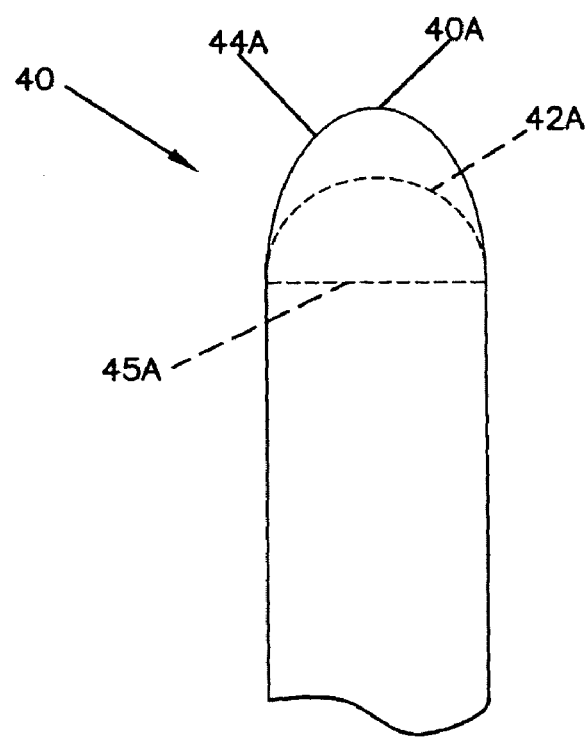
FIG. 11 is a top view of a second embodiment of a sensor strip.
Figure 12:
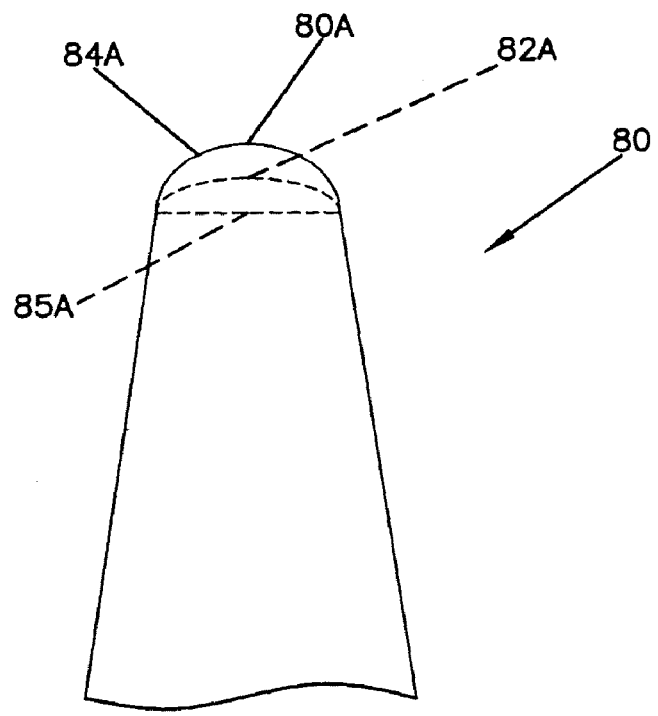
FIG. 12 is a top view of a third embodiment of a sensor strip.

Referring to FIGS. 11 and 12, two variations of sensor strip 10 are illustrated as sensor strips 40 and 80. Each of sensor strips 40 and 80 has a distal end that is rounded, curved, or otherwise has a radius associated therewith. Additionally, sensor strip 80 of FIG. 12 has a taper associated therewith, progressing from the proximal end to the distal end. Sensor strip 40 includes a sample receiving, distal end 40A defined by distal end 44A of the second substrate. Distal end 44A overhangs first substrate's distal end 42A and spacer's distal end 45A. Sensor strip 80 includes a sample receiving, distal end 80A defined by distal end 84A of the second substrate. Distal end 84A overhangs first substrate's distal end 82A and spacer's distal end 85A.

Figure 13:
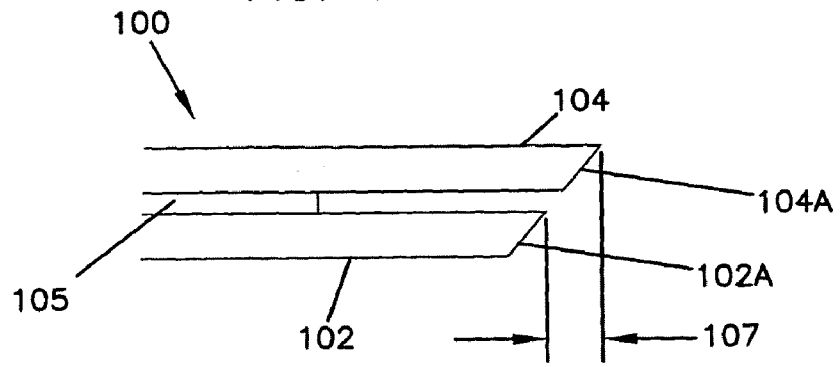
FIG. 13 is a side view of a second embodiment of an electrochemical sensor strip in accordance with the principles of the present invention, similar to the first embodiment.

Referring to FIG. 13, a sensor strip 100, a variation of sensor strip 10, is illustrated. Sensor strip 100 includes a first substrate 102 having a distal end 102A and a second substrate 104 having a distal end 104A. Positioned between substrates 102, 104 is spacer 105. Sensor strip 100 is similar to sensor strip 10 except that distal ends 102A, 104A have an angle associated therewith. Sensor strip 100 includes overhang 107, which is the overhang of distal end 104A past end 102A. Angled distal ends 102A, 104A can be formed, for example, by slicing off a portion of sensor strip 10. The angled end of sensor strip 100 may facilitate filling of the sample chamber, such as when sensor strip 100 is pivoted about its distal end (that is, as distal ends 102A, 104A are lowered or otherwise moved over a biological fluid to be analyzed).

Sensing Chemistry

In addition to working electrode 22, sensing chemistry material(s) may be provided in sample chamber 20 for the analysis of the analyte. Sensing chemistry material facilitates the transfer of electrons between working electrode 22 and the analyte in the sample. Any suitable sensing chemistry may be used in sensor strip 10; the sensing chemistry may include one or more materials.

The sensing chemistry may be diffusible or leachable, or non-diffusible or non-leachable. For purposes of discussion herein, the term "diffusible" will be used to represent "diffusible or leachable" and the term "non-diffusible" will be used to represent "non-diffusible or non-leachable" and variations thereof. Placement of sensing chemistry components may depend at least in part on whether they are diffusible or not. For example, both non-diffusible and/or diffusible component(s) may form a sensing layer on working electrode 22. Alternatively, one or more diffusible components may be present on any surface in sample chamber 20 prior to the introduction of the sample to be analyzed. As another example, one or more diffusible component(s) may be placed in the sample prior to introduction of the sample into sample chamber 20.

Electron Transfer Agent

The sensing chemistry generally includes an electron transfer agent that facilitates the transfer of electrons to or from the analyte. The electron transfer agent may be diffusible or non-diffusible, and may be present on working electrode 22 as a layer. One example of a suitable electron transfer agent is an enzyme which catalyzes a reaction of the analyte. For example, a glucose oxidase or glucose dehydrogenase, such as pyrroloquinoline quinone glucose dehydrogenase (PQQ), is used when the analyte is glucose. Other enzymes can be used for other analytes.

The electron transfer agent, whether it is diffusible or not, facilitates a current between working electrode 22 and the analyte and enables the electrochemical analysis of molecules. The agent facilitates the transfer electrons between the electrode and the analyte.

Redox Mediator

The sensing chemistry may, additionally to or alternatively to the electron transfer agent, include a redox mediator. Certain embodiments use a redox mediator that is a transition metal compound or complex. Examples of suitable transition metal compounds or complexes include osmium, ruthenium, iron, and cobalt compounds or complexes. In these complexes, the transition metal is coordinatively bound to one or more ligands, which are typically mono-, di-, tri-, or tetradentate. The redox mediator can be a polymeric redox mediator, or, a redox polymer (i.e., a polymer having one or more redox species). Examples of suitable redox mediators and redox polymer are disclosed in U.S. Pat. No. 6,338,790, for example, and in U.S. Pat. Nos. 6,605,200 and 6,605,201.

If the redox mediator is non-diffusible, then the redox mediator may be disposed on working electrode 22 as a layer. In an embodiment having a redox mediator and an electron transfer agent, if the redox mediator and electron transfer agent are both non-leachable, then both components are disposed on working electrode 22 as individual layers, or combined and applied as a single layer.

The redox mediator, whether it is diffusible or not, mediates a current between working electrode 22 and the analyte and enables the electrochemical analysis of molecules which may not be suited for direct electrochemical reaction on an electrode. The mediator functions as an agent to transfer electrons between the electrode and the analyte.

Manufacture of the Sensors

Sensor strips 10, 100, described above, are sandwiched or layered constructions having substrates 12, 14 spaced apart, such as by spacer 15. Such a construction may be made by laminating the various layers together, in any suitable manner. An alternate method for making sensor strips 10, 100 and other sensors in accordance with the invention, is to mold the sensors.

Molding could include positioning at least two spaced apart electrically conductive electrodes (e.g., wires) in a mold, and molding a body of insulative material around the electrodes, with one end having therein means for receiving a fluid sample. More specifically, molding could include positioning at least two spaced apart electrically conductive electrodes (e.g., wires) in a mold, before or after molding, treating at least one of the electrodes with one or more chemicals to change the electrical properties of the treated electrode upon contact with a fluid sample, and molding a body of insulative material around the electrodes with one end having therein means for receiving a fluid sample. The body can be molded in multiple pieces, e.g., two pieces, with a body and end cap for attaching to one another after the molding is completed, or in a single piece.

A sensor may be made by determining a suitable length of an overhang for a sensor and manufacturing the sensor so that it includes such an overhang. For example, a sensor may be made by positioning electrodes on one or more substrates, the substrates including a first substrate having a first length and a second substrate having a second length, contacting at least a portion of at least one electrode with sensing reagent(s) and configuring the sensor by positioning a spacer between the two substrates to maintain the substrates in a fixed, layered orientation relative to each other. The substrates are positioned so that the additional length of the first sensor resides at the distal or sample receiving end of the sensor.

In some embodiments, whether the substrates are the same length or not, the substrates may be displaced relative to each other along their longitudinal axes so that one of the substrates, e.g., the top substrate, extends a distance beyond the end of the other (e.g., bottom substrate) at the sample receiving end to provide the overhang. Contact pads may be positioned at the proximal end.

Application of the Sensor

A common use for the analyte sensor of the present invention, such as sensor strip 10, 100, is for the determination of analyte concentration in a biological fluid, such as glucose concentration in blood, interstitial fluid, and the like, in a patient or other user. Sensor strips 10 may be available at pharmacies, hospitals, clinics, from doctors, and other sources of medical devices. Multiple sensor strips 10, 100 may be packaged together and sold as a single unit; e.g., a package of 25, 50, or 100 strips.

Sensor strips 10 can be used for an electrochemical assay, or, for a photometric test. Sensor strips 10 are generally configured for use with an electrical meter, which may be connectable to various electronics. A meter may be available at generally the same locations as sensor strips 10, and sometimes may be packaged together with sensor strips 10, e.g., as a kit.

Examples of suitable electronics connectable to the meter include a data processing terminal, such as a personal computer (PC), a portable computer such as a laptop or a handheld device (e.g., personal digital assistants (PDAs)), and the like. The electronics are configured for data communication with the receiver via a wired or a wireless connection. Additionally, the electronics may further be connected to a data network (not shown) for storing, retrieving and updating data corresponding to the detected glucose level of the user.

The various devices connected to the meter may wirelessly communicate with a server device, e.g., using a common standard such as 802.11 or Bluetooth RF protocol, or an IrDA infrared protocol. The server device could be another portable device, such as a Personal Digital Assistant (PDA) or notebook computer, or a larger device such as a desktop computer, appliance, etc. In some embodiments, the server device does have a display, such as a liquid crystal display (LCD), as well as an input device, such as buttons, a keyboard, mouse or touch-screen. With such an arrangement, the user can control the meter indirectly by interacting with the user interface(s) of the server device, which in turn interacts with the meter across a wireless link.

The server device can also communicate with another device, such as for sending glucose data from the meter and/or the service device to a data storage or computer. For example, the service device could send and/or receive instructions (e.g., an insulin pump protocol) from a health care provider computer. Examples of such communications include a PDA synching data with a personal computer (PC), a mobile phone communicating over a cellular network with a computer at the other end, or a household appliance communicating with a computer system at a physician's office.

A lancing device or other mechanism to obtain a sample of biological fluid, e.g., blood, from the patient or user may also be available at generally the same locations as sensor strips 10 and the meter, and sometimes may be packaged together with sensor strips 10 and/or meter, e.g., as a kit.

Sensor strips 10, 100 are particularly suited for inclusion in an 'integrated device', i.e., a device which has the sensor and a second element, such as a meter or a lancing device, in the device. Other sensor strips, such as those having no overhang 17, but where cantilever 16 is generally equal to extension 18, would also be suitable for inclusion in an integrated device. The integrated device may be based on providing an electrochemical assay or a photometric assay. In some embodiments, sensor strips 10, 100 may be integrated with both a meter and a lancing device. Having multiple elements together in one device reduces the number of devices needed to obtain an analyte level and facilitates the sampling process.

For example, embodiments may include a housing that includes one or more of the subject strips, a skin piercing element and a processor for determining the concentration of an analyte in a sample applied to the strip. A plurality of strips 10, 100 may be retained in a cassette in the housing interior and, upon actuation by a user, a single strip 10, 100 may be dispensed from the cassette so that at least a portion extends out of the housing for use.

Operation of the Sensor Strip

In use, a sample of biological fluid is provided into the sample chamber of the sensor, where the level of analyte is determined. In many embodiments, it is the level of glucose in blood, interstitial fluid, and the like, that is determined. Also in many embodiments, the source of the biological fluid is a drop of blood drawn from a patient, e.g., after piercing the patient's skin with a lancing device or the like, which may be present in an integrated device, together with the sensor strip.

Embodiments of the subject methods may include contacting the sensor (e.g., an overhang of the sensor) with the skin of a user to form a capillary space and transferring a volume of fluid from a skin incision within the thus-formed capillary space to the sample chamber of the sensor. Accordingly, bodily fluid may be first contacted with at least a portion of one of the substrates of the sensor (e.g., the overhang of a top substrate) prior to being contacted with the other substrate and/or sample chamber.

Figure 14A:
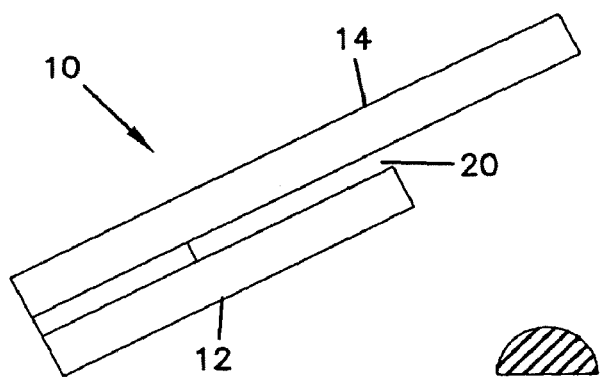
FIGS. 14A, 14B and 14C are schematic illustrations of a process for filling a sensor strip of FIGS. 1, 2, 3 and 10 with biological fluid.
Figure 14B:
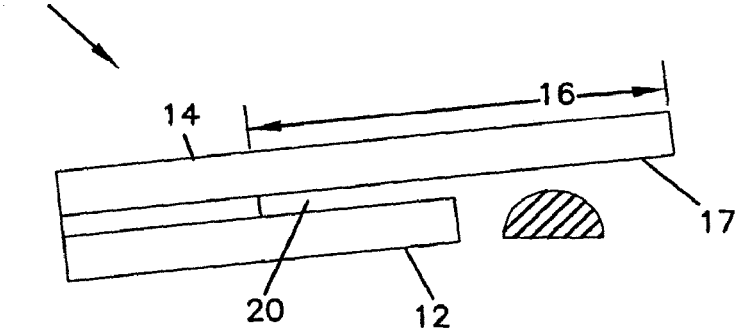
Figure 14C:
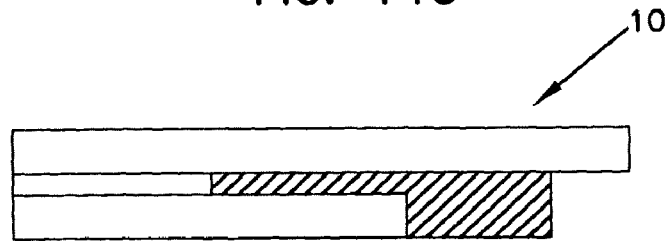

FIGS. 14A, 14B and 14C illustrate step-wise the filling of sensor strip 10 according to an embodiment of the subject invention, which is facilitated by capillary action provided by the sensor overhang. In FIG. 14A, sensor strip 10 is positioned at an angle above a drop of biological fluid such as blood to be analyzed. FIG. 14B illustrates sensor strip 10 being pivotally lowered onto the drop of blood, so that substrate 14, and particularly overhang 17, is positioned adjacent, e.g., over, the blood. Sensor strip 10 is pivoted at or close to its proximal end. In this position, when sensor strip 10 is lowered further, a capillary space having a volume as described above, is formed by the overhang and the skin. The blood sample will directly contact substrate 14 at cantilever 16, particularly at overhang 17. Upon contact with the blood, in FIG. 14C, a portion of the blood sample is drawn into sample chamber 20 due to capillary action, which is a function of the surface characteristics and dimensions of sensor strip 10, particularly, the space between overhang 17 and the surface on which the blood sits. The surface of substrate 14 may be hydrophilic, which facilitates drawing the blood into sample chamber 20. It is understandable that the larger the overhang, the easier to fill sample chamber 20.

Figure 15A:
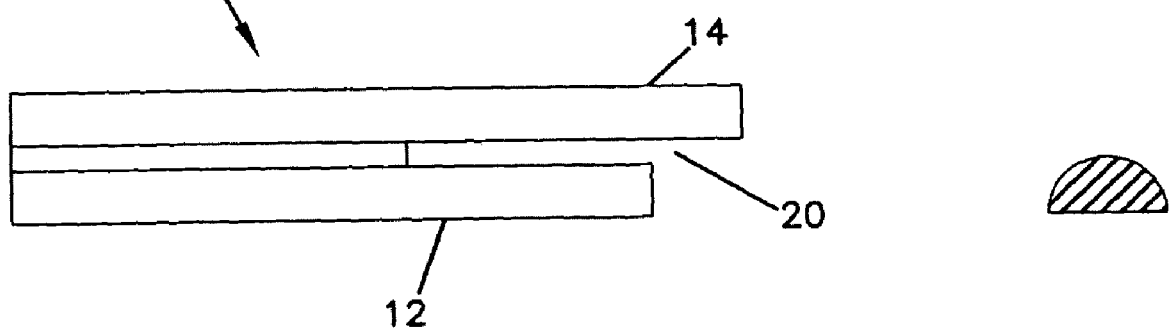
FIGS. 15A, 15B and 15C are schematic illustrations of an alternate process for filling a sensor strip of FIGS. 1, 2, 3 and 10 with biological fluid.
Figure 15B:
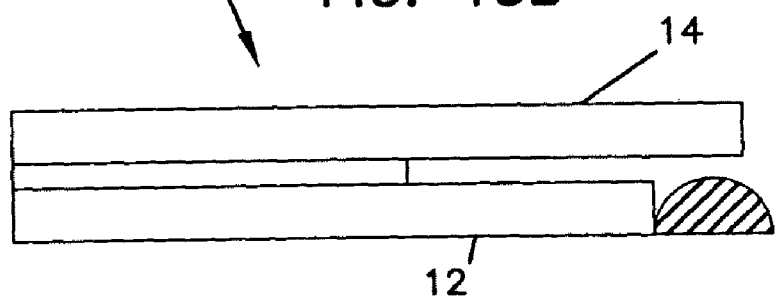
Figure 15C:
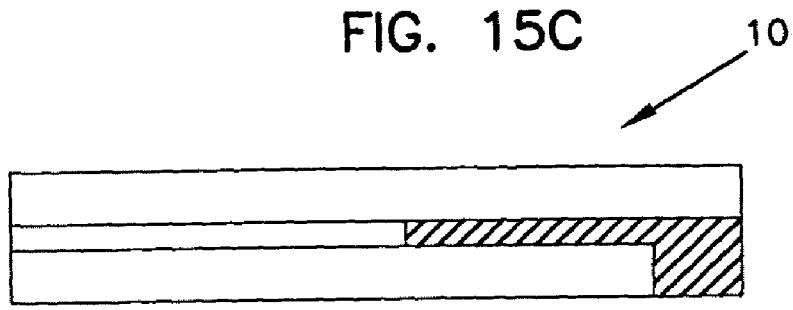

FIGS. 15A, 15B and 15C illustrate step-wise another embodiment of the subject methods for filling of sensor strip 10. In FIG. 15A, sensor strip 10 is positioned generally planar to a drop of bodily fluid, e.g., blood, interstitial fluid, or the like, to be analyzed; sensor strip 10 and the blood are typically on the same supporting surface. FIG. 15B illustrates sensor strip 10 being pushed or otherwise moved into the drop of blood, so that sample chamber 20 is positioned at a level with the blood. In this position, when sensor strip 10 is pushed further, the blood sample will directly contact side 20A (see FIG. 10) of sample chamber 20. Upon contact with the blood, in FIG. 15C, a portion of the blood sample is drawn into sample chamber 20 due to capillary action between overhang 17 and the surface on which the blood drop sits; this capillary action is a function of the surface characteristics and dimensions of sensor strip 10, particularly overhang 17. The capillary chamber of FIG. 15C formed by the overhang is shown completely filled, as is the sample chamber, for exemplary purposes only and is in no way intended to limit the scope of the invention. It is to be understood that the capillary chamber and/or the sample chamber need not fill completely or need not be completely or partially filled simultaneously. The filling of the sample chamber may cause partial to complete emptying of the sample from the capillary chamber.

In a combination of the two above-described methods, sensor strip 100 of FIG. 13 may be filled by sliding strip 100 toward the blood sample and then pivoting strip 100 about or near its distal end, to fill the sample chamber. Blood would be drawn into the sample chamber by capillary action.

Sensor strip 10, 100 may be operated with or without applying a potential to electrodes 22, 24. In one embodiment, the electrochemical reaction occurs spontaneously and a potential need not be applied between working electrode 22 and counter electrode(s) 24. In another embodiment, a potential is applied between working electrode 22 and counter electrode(s) 24. The potential may be constant or not. The magnitude of the potential is dependent on the redox mediator.

The invention of this disclosure is not directed to the potential utilized, or lack thereof, in use of sensor strip 10, 100. Details regarding potential as related to the sensing chemistry and the electrodes are discussed, for example, in U.S. Pat. No. 6,338,790.

In any event, before, during or after sample is contacted with the sample chamber, the sensor is coupled to a meter and the concentration of an analyte in the sample, e.g., glucose, is be determined.

The invention has been described with reference to various specific and preferred embodiments and techniques. However, it will be apparent to one of ordinary skill in the art that many variations and modifications may be made while remaining within the spirit and scope of the invention.

All patents, applications and other references in this specification are indicative of the level of ordinary skill in the art to which this invention pertains. All patents, patent applications and other references are herein incorporated by reference to the same extent as if each individual patent, application or reference was specifically and individually incorporated by reference.

We claim:

1. A cantilevered analyte sensor for determining the concentration of a ketone body in a sample, the sensor comprising:
    a first substrate and a second substrate;
    a working electrode positioned on one of the first substrate or the second substrate;
    a sample chamber positioned between the first and second substrates; and
    an overhanging substrate wall at a sample receiving end of the sensor; wherein the sample chamber comprises at least two unbounded sides at the sample receiving end of the sensor.

2. The sensor of claim 1, wherein the overhanging substrate wall provides a capillary volume that ranges from about 10 nL to about 10,000 nL.

3. The sensor of claim 2, wherein the capillary volume ranges from about 100 nL to about 1000 nL.

4. The sensor of claim 1, wherein about 10% to about 95% of the perimeter of the sample chamber is unbounded.

5. The sensor of claim 4, wherein about 50% to about 95% of the perimeter of the sample chamber is unbounded.

6. The sensor of claim 1, wherein the sample chamber comprises three unbounded sides.

7. The sensor of claim 1, wherein the overhang ranges from about 0.05% to about 50% of the length of the sensor.

8. The sensor of claim 1, wherein the overhang has a surface area that ranges from about 0.1 mm$^2$ to 1 cm$^2$.

9. The sensor of claim 1, wherein the overhang has a length of at least about 0.1 mm.

10. The sensor of claim 9, wherein the overhang has a length of at least about 1 mm.

11. The sensor of claim 1, wherein the overhang is contiguous with the second substrate.

12. The sensor of claim 11, wherein the length of the second substrate is greater than the length of the first substrate.

13. The sensor of claim 1, wherein the substrates are displaced along their longitudinal axes.

14. The sensor of claim 1, wherein the sample chamber has a volume of no more than about 1 microliter.

15. The sensor of claim 14, wherein the sample chamber has a volume of no more than about 0.5 microliter.

16. The sensor of claim 15, wherein the sample chamber has a volume of no more than about 0.1 microliter.

17. A sensor for determining the concentration of a ketone body in a sample, the sensor comprising:
    a first substrate and a second substrate;
    a working electrode positioned on one of the first substrate or the second substrate;
    a sample chamber positioned between the first and second substrates; and
    an overhang configured to form a capillary chamber when positioned in opposition to a surface,
    wherein the sample chamber comprises at least two unbounded sides at a sample receiving end of the sensor.

18. The sensor of claim 17, wherein the capillary chamber has a volume that ranges from about 10 nL to about 10,000 nL.

19. The sensor of claim 18, wherein the volume ranges from about 100 nL to about 1000 nL.

20. The sensor of claim 17, wherein the sensor is a cantilever sensor.

21. An integrated system for the determination of ketone bodies in biological fluid, the system comprising:
a housing having an interior space;
at least one cantilevered analyte sensor for determining the concentration of a ketone body in a sample positioned in the interior space, the sensor comprising:
a first substrate and a second substrate;
a working electrode positioned on one of the first substrate or the second substrate;
a sample chamber positioned between the first and second substrates; and
an overhanging substrate wall at a sample receiving end of the sensor,
wherein the sample chamber comprises at least two unbounded sides at the sample receiving end of the sensor; and
a processor for determining the concentration of a ketone body applied to a sensor.

22. The integrated system of claim 21, further comprising a skin piercing element.

23. A system for determining the concentration of a ketone body in a sample, the system comprising:
a cantilevered analyte sensor for determining the concentration of a ketone body in a sample, the sensor comprising a first substrate and a second substrate;
a working electrode positioned on one of the first substrate or the second substrate;
a sample chamber positioned between the first and second substrates;
and an overhanging substrate wall at a sample receiving end of the sensor, wherein the sample chamber comprises at least two unbounded sides at the sample receiving end of the sensor; and
a meter.

24. A method of providing a sample to a sample chamber of a ketone body sensor comprising:
contacting an overhang at a sample receiving end of the sensor with the sample to provide sample to the sample chamber, wherein the analyte sensor comprises:
a first substrate and a second substrate;
a working electrode positioned on one of the first substrate or the second substrate;
the sample chamber positioned between the first and second substrate; and
an overhanging substrate wall at a sample receiving end of the sensor
wherein the sample chamber comprises at least two unbounded sides at the sample receiving end of the sensor.

25. The method of claim 24, wherein the contact comprises positioning the overhang in opposition to a surface to provide a capillary volume by the overhang and the surface.

26. The method of claim 25, wherein the capillary volume ranges from about 10 nL to about 10,000 nL.

27. The method of claim 26, wherein the capillary volume ranges from about 100 nL to about 1000 nL.

28. The method of claim 24, further comprising determining the concentration of a ketone body in at least a portion of the sample in the sample chamber.

29. The method of claim 28, wherein the ketone body concentration is determined using about 1 microliter of sample or less.

30. The method of claim 28, wherein the ketone body concentration is determined using coulometry.

31. The method of claim 28, wherein the ketone body concentration is determined using amperometry.

32. The method of claim 28, wherein the ketone body concentration is determined using potentiometry.

33. The method of claim 28, wherein the ketone body concentration is determined using photometry.

34. The method of claim 24, wherein the overhang is contiguous with the second substrate, and the contacting comprises first contacting the sample with the overhang and then contacting the first substrate and/or the sample chamber with the sample.

35. A kit comprising:
a cantilevered analyte sensor for determining the concentration of a ketone body in a sample, the sensor comprising:
a first substrate and a second substrate;
a working electrode positioned on one of the first substrate or the second substrate;
a sample chamber positioned between the first and second substrates; and
an overhanging substrate wall at a sample receiving end of the sensor, wherein the sample chamber comprises at least two unbounded sides at the sample receiving end of the sensor; and
a meter.

* * * * *

UNITED STATES PATENT AND TRADEMARK OFFICE
CERTIFICATE OF CORRECTION

| | | |
|---|---|---|
| PATENT NO. | : 7,993,505 B2 | Page 1 of 1 |
| APPLICATION NO. | : 12/463213 | |
| DATED | : August 9, 2011 | |
| INVENTOR(S) | : Benjamin J. Feldman | |

It is certified that error appears in the above-identified patent and that said Letters Patent is hereby corrected as shown below:

On the Title Page Item (73) please correct the spelling of the Assignee to read --Abbott Diabetes Care Inc.--

Signed and Sealed this
Twenty-sixth Day of June, 2012

David J. Kappos
*Director of the United States Patent and Trademark Office*